US00PP29974P2

(12) United States Plant Patent
Pieters

(10) Patent No.: US PP29,974 P2
(45) Date of Patent: Dec. 11, 2018

(54) ***CHRYSANTHEMUM* PLANT NAMED 'VENOS YELLOW'**

(50) Latin Name: *Chrysanthemum X morifolium*
Varietal Denomination: Venos Yellow

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 15/731,854

(22) Filed: Aug. 15, 2017

(51) Int. Cl.
*A01H 5/02* (2018.01)

(52) U.S. Cl.
USPC ..... Plt./289
CPC ..... *A01H 5/0255* (2013.01)

(58) Field of Classification Search
USPC ..... Plt./289
CPC ..... A01H 5/0255
See application file for complete search history.

(56) References Cited

PUBLICATIONS https://issuu.com/hfmichell/docs/2018_michells_catalog-final; Jul. 19, 2017; 2 pages.*

* cited by examiner

*Primary Examiner* — Kent L Bell
(74) *Attorney, Agent, or Firm* — C. A. Whealy

(57) ABSTRACT

A new and distinct cultivar of *Chrysanthemum* plant named 'Venos Yellow', characterized by its upright, outwardly spreading and uniformly rounded plant habit; moderately vigorous growth habit; freely branching habit; dense and full plant habit; dark green-colored leaves; uniform and freely flowering habit; long flowering period; and relatively large decorative-type inflorescences with dark yellow-colored ray florets.

1 Drawing Sheet

Botanical designation: *Chrysanthemum* X *morifolium*.
Cultivar denomination: 'VENOS YELLOW'.

BACKGROUND OF THE INVENTION

The present invention relates to a new and distinct cultivar of *Chrysanthemum* plant, botanically known as *Chrysanthemum* X *morifolium* and hereinafter referred to by the name 'Venos Yellow'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in Oostnieuwkerke, Belgium in September, 2011 of *Chrysanthemum* X *morifolium* 'Axima Yellow', not patented, as the female, or seed, parent with *Chrysanthemum* X *morifolium* 'Cortona', not patented, as the male, or pollen, parent. The new *Chrysanthemum* plant was discovered and selected by the Inventor as a flowering plant from within the progeny of the stated cross-pollination in a controlled greenhouse environment in Oostnieuwkerke, Belgium in September, 2012.

Asexual reproduction of the new *Chrysanthemum* plant by vegetative terminal cuttings was first conducted in a controlled greenhouse environment in Oostnieuwkerke, Belgium in September, 2015. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Venos Yellow'. These characteristics in combination distinguish 'Venos Yellow' as a new and distinct *Chrysanthemum* plant:

1. Upright, outwardly spreading and uniformly rounded plant habit; moderately vigorous growth habit.
2. Freely branching habit; dense and full plant habit.
3. Dark green-colored leaves.
4. Uniform and freely flowering habit.
5. Long flowering period.
6. Relatively large decorative-type inflorescences with dark yellow-colored ray florets.

Plants of the new *Chrysanthemum* differ from the female parent, 'Axima Yellow', in the following characteristics:

1. Plants of the new *Chrysanthemum* are more uniform in plant shape than plants of 'Axima Yellow'.
2. Plants of the new *Chrysanthemum* flower later than plants of 'Axima Yellow'.
3. Ray florets of plants of the new *Chrysanthemum* are slightly lighter yellow in color than ray florets of plants of 'Axima Yellow'.

Plants of the new *Chrysanthemum* differ from the male parent, 'Cortona', in the following characteristics:

1. Plants of the new *Chrysanthemum* are more uniform in plant shape than plants of 'Cortona'.
2. Inflorescences of plants of the new *Chrysanthemum* are fully decorative in form whereas inflorescences of plants of 'Cortona' are semi-decorative in form.
3. Ray florets of plants of the new *Chrysanthemum* are lighter yellow in color than ray florets of plants of 'Cortona'.

Plants of the new *Chrysanthemum* can be compared to plants of *Chrysanthemum* X *morifolium* 'Allegra Yellow', disclosed in U.S. Plant Pat. No. 21,785. In side-by-side comparisons, plants of the new *Chrysanthemum* differ from plants of 'Allegra Yellow' in the following characteristics:

1. Plants of the new *Chrysanthemum* are more spherical than and not as flat as plants of 'Allegra Yellow'.
2. Plants of the new *Chrysanthemum* flower later than plants of 'Allegra Yellow'.
3. Inflorescences of plants of the new *Chrysanthemum* are longer lasting than inflorescences of plants of 'Allegra Yellow'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Venos Yellow' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum* X *morifolium* 'Venos Yellow'.

Parentage:

*Female, or seed, parent.*—*Chrysanthemum* X *morifolium* 'Axima Yellow', not patented.

*Male, or pollen, parent.*—*Chrysanthemum* X *morifolium* 'Cortona', not patented.

Propagation:

*Type.*—Vegetative terminal cuttings.

*Time to initiate roots, summer.*—About 14 days at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots dependent on substrate composition, water quality, fertilizer, substrate temperature and age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants nearly spherical in overall shape; very freely branching habit, about 20 primary lateral branches develop per plant, each primary lateral branch with multiple secondary branches; pinching is not required, however, will enhance lateral branch development; dense and full plant habit; moderately vigorous growth habit; medium growth rate.

*Plant height.*—About 40 cm.

*Plant width.*—About 50 cm.

*Lateral branches.*—Length: About 30 cm. Diameter: About 2 mm to 3 mm. Internode length: About 2 cm to 2.5 cm. Strength: Strong, flexible. Aspect: Upright to outwardly spreading. Texture and luster: Fine pubescence; longitudinally ridged; matte. Color: Close to 141A.

*Leaves.*—Arrangement: Alternate, simple. Length: About 4.5 cm to 6.5 cm. Width: About 2.5 cm to 3.5 cm. Apex: Rounded. Base: Attenuate. Margin: Palmately lobed and serrate, sinuses between lateral lobes divergent to parallel. Texture and luster, upper and lower surfaces: Slightly pubescent; matte. Color: Developing leaves, upper surface: Close to 141A. Developing leaves, lower surface: Close to 139C. Fully expanded leaves, upper surface: Close to 137A; venation, close to 148C. Fully expanded leaves, lower surface: Close to 137C; venation, close to 147B to 147C. Petioles: Length: About 1 cm. Diameter: About 2 mm. Texture and luster, upper and lower surfaces: Slightly pubescent; slightly rough; matte. Color, upper surface: Close to 137A. Color, lower surface: Close to 137C.

Inflorescence description:

*Appearance.*—Decorative-type inflorescence form; inflorescences borne on terminals above foliar plane; disc and ray florets arranged acropetally on a capitulum.

*Fragrance.*—Faintly fragrant, pungent.

*Flowering time.*—Under natural season conditions, plants flower in early to mid-September in Belgium; response time is about seven weeks.

*Postproduction longevity.*—Inflorescences maintain good color and substance for about 38 to 40 days on the plant grown in an outdoor nursery; inflorescences persistent.

*Quantity of inflorescences.*—Freely flowering habit with about 20 to 25 inflorescences developing per lateral branch with numerous inflorescences developing per plant.

*Inflorescence buds.*—Height: About 7 mm. Diameter: About 1 cm. Shape: Globular. Texture and luster: Smooth, glabrous; matte. Color: Close to 163B.

*Inflorescence size and shape.*—Diameter: Relatively large, about 5.5 cm. Depth (height): About 4 cm. Disc diameter: About 5 mm.

*Receptacles*.—Diameter: About 3 mm. Height: About 2.5 mm to 3 mm. Shape: Circular; raised dome. Texture and luster: Smooth, glabrous; matte. Color: Close to 144B.

*Ray florets*.—Quantity and arrangement: About 125 to 150 ray florets per inflorescence arranged in about seven whorls. Length: About 3.5 cm to 5 cm. Width: About 8 mm. Shape: Oval. Apex: Rounded. Base: Attenuate. Margin: Entire. Aspect: Mostly flat. Texture and luster, upper and lower surfaces: Smooth, glabrous; matte. Color: When opening and fully opened, upper surface: Close to 7A; color becoming closer to 6A with development. When opening and fully opened, lower surface: Close to 6A; color does not fade with development.

*Disc florets*.—Quantity and arrangement: About 50 to 60 disc florets per inflorescence and spirally massed at the center of the receptacle; mostly inconspicuous. Length: About 3 mm. Diameter: About 0.5 mm to 1 mm. Shape: Tubular, elongated; apices acute. Texture and luster: Smooth, glabrous; glossy. Color: When opening: Close to 145A. Fully opened: Close to 12A.

*Phyllaries*.—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire; translucent. Texture and luster, upper and lower surfaces: Smooth, glabrous; matte. Color, upper surface: Close to 137A. Color, lower surface: Close to N137B.

*Peduncles*.—Length, terminal peduncle: About 5 cm. Length, fourth peduncle: About 7 cm. Length, seventh peduncle: About 7 cm. Diameter: About 2.5 mm. Angle, lateral peduncles: About 30° from vertical. Strength: Moderately strong. Texture and luster: Slightly pubescent; matte. Color: Close to 146B.

*Reproductive organs*.—Androecium: None observed. Gynoecium: None observed.

*Seeds and fruits*.—Seed and fruit production have not been observed on plants of the new *Chrysanthemum* to date.

Disease & pest resistance: Resistance to pathogens and pests common to *Chrysanthemum* plants has not been observed on plants of the new *Chrysanthemum* grown under commercial production conditions to date.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Venos Yellow' as illustrated and described.

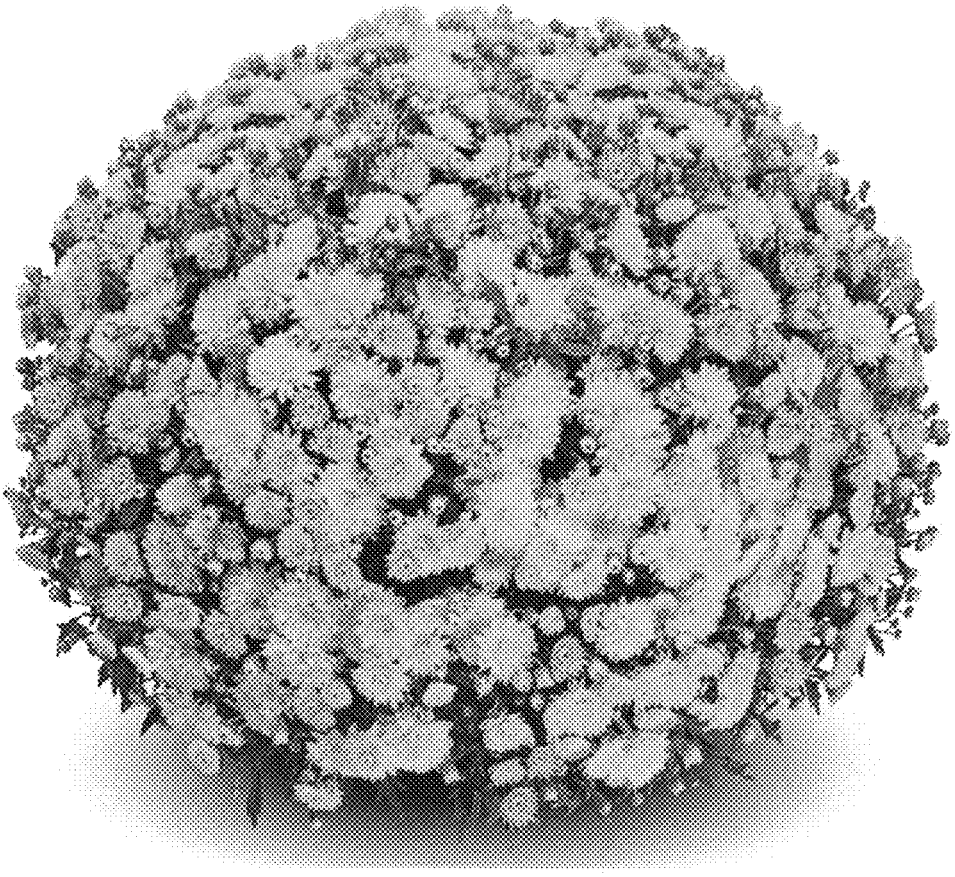

* * * * *